(12) United States Patent
Schmenger et al.

(10) Patent No.: US 7,125,427 B2
(45) Date of Patent: Oct. 24, 2006

(54) COLORING AGENT FOR KERATIN FIBERS

(75) Inventors: Juergen Schmenger, Weiterstadt (DE); Wilhelm Abels, Simi Valley, CA (US); Manfred Schmitt, Heppenheim (DE); Gabriele Hess, Erzhausen (DE); Anke Frank, Griesheim (DE)

(73) Assignee: Wella AG, Darmstadt (DE)

( * ) Notice: Subject to any disclaimer, the term of this patent is extended or adjusted under 35 U.S.C. 154(b) by 298 days.

(21) Appl. No.: 10/399,919

(22) PCT Filed: Jul. 12, 2002

(86) PCT No.: PCT/EP02/07763

§ 371 (c)(1), (2), (4) Date: Jul. 14, 2003

(87) PCT Pub. No.: WO03/017956

PCT Pub. Date: Mar. 6, 2003

(65) Prior Publication Data

US 2004/0098815 A1    May 27, 2004

(30) Foreign Application Priority Data

Aug. 28, 2001 (DE) .......................... 201 14 179 U

(51) Int. Cl.
*A61K 7/13* (2006.01)
(52) U.S. Cl. ................... 8/405; 8/406; 8/552; 8/602; 8/611; 524/590; 525/406
(58) Field of Classification Search ............ 8/405, 8/406, 552, 602, 611; 524/590; 525/406
See application file for complete search history.

(56) References Cited

U.S. PATENT DOCUMENTS 6,156,076 A    12/2000 Casperson ................. 8/406
6,436,151 B1 *  8/2002 Cottard et al. .............. 8/406
6,916,344 B1    7/2005 Allard et al.
2002/0000012 A1 *  1/2002 Schmenger et al. ......... 8/405

FOREIGN PATENT DOCUMENTS

| DE | 200 18 140 U | 2/2001 |
| EP | 1 093 806 A | 4/2001 |
| FR | 2 802 089 A | 6/2001 |
| FR | 2 802 090 A | 6/2001 |
| FR | 2 802 092 A | 6/2001 |
| WO | 96 40815 A | 12/1996 |
| WO | WO 96/40815 | * 12/1996 |
| WO | 01/41718 | 6/2001 |
| WO | 01/41723 A1 | 6/2001 |

OTHER PUBLICATIONS

E. Sagarin, "Cosmetics, Science and Technoly", Interscience Publishers Inc., New York, 1957, pp. 503-507.
H. Janistyn "Handbuch der Kosmetika und Riechstoffe", Band 3, 1973, pp. 388-397.
K. Schrader "Grundlagen und Rezepturen der Kosmetika", 2. Auflage, 1989, pp. 782-815.
International Cosmetic Ingredient Dictionary and Handbook, Tenth Edition, 2004, p. 1332.

* cited by examiner

*Primary Examiner*—Eisa Elhilo
(74) *Attorney, Agent, or Firm*—Michael J. Striker

(57) ABSTRACT

The colorants for keratin fibers are based on oxidation dye precursors and/or direct dyes and contain a combination of (a) at least one nonionic, amphiphilic associative thickener, (b) at least one fatty alcohol that is liquid at 25° C. and (c) PEG-150/stearyl alcohol/SMDI copolymer in a suitable cosmetic carrier.

13 Claims, No Drawings

COLORING AGENT FOR KERATIN FIBERS

BACKGROUND OF THE INVENTION

The object of the invention are colorants for keratin fibers, particularly human hair, that contain direct and/or oxidation dyes and a special thickener combination, as well as a method for coloring hair by use of such colorants, Coloring preparations are usually in the form of aqueous—preferably thickened—solutions or emulsions and contain besides dyes, for example, fatty alcohols and/or other oil components, emulsifiers and surfactants as well as optionally alcohols. Oxidation dyes as a rule consist of two components (i) the dye carrier composition containing the dyes and (ii) the oxidation dye preparation, said components being mixed with one another shortly before use and then applied to the hair to be dyed. Mixing will produce a higher or lower viscosity, depending on the viscosity and mixing ratio of the two components. In particular, good adhesion of the colorant is achieved in this case if the colorant has a higher viscosity. In addition, the hair dresser often needs for her work higher viscosities, for example for special strand or sheet techniques and when special work is to be done with the dye brush or the highlighting brush.

Hence, a great need existed for economical thickening of the dye carrier composition that would ensure good miscibility of said dye carrier composition with the oxidant and would afford colorants with good adhesion properties and coloring characteristics.

The use of nonionic, amphiphilic associative thickeners for thickening hair colorants is known from WO 01/41723. The colorants described therein, however, are not satisfactory in all respects as regards their viscosity, adhesion to hair and coloring properties. For example, the viscosity-forming properties deteriorate after a storage period of only a few weeks. Moreover, the colorants described in WO 01/41723 have a honey-like consistency which allows the coloring composition to run off the hair. Another drawback is that high dye concentrations are incompatible with the associative thickeners.

SUMMARY OF THE INVENTION

In this respect, we have now found that the aforesaid drawbacks of associative thickeners can be eliminated by use of a combination of such associative thickeners with a fatty alcohol and an additional thickener based on a nonionic polyol modified so as to be hydrophobic.

The object of the present invention therefore is an agent for coloring keratin fibers, particularly hair, based on oxidation dye precursors and/or direct dyes, characterized in that it contains in a suitable cosmetic carrier a combination of (a) at least one nonionic, amphiphilic associative thickener,
(b) at least one fatty alcohol that is liquid at 25° C. and
(c) a PEG-150/stearyl/SMDI copolymer.

The nonionic, amphiphilic associative thickener is contained in the composition of the invention preferably in an amount from about 0.01 to 2.5 wt. % and particularly from about 0.1 to 1 wt. % (based on the active substance).

The nonionic, amphiphilic associative thickener is a polymer that contains both hydrophilic and hydrophobic groups. Associative thickeners are water-soluble polymers containing surfactant-like hydrophobic components which in a hydrophilic, particularly aqueous, medium are capable of undergoing association, namely interaction, with themselves as well as with other hydrophobic substances. The resulting associative network causes the medium to thicken or gel.

Typically, associative thickeners are prepared by polymerization of polyethylene oxide prepolymers and at least difunctional polycondensable substances, for example isocyanates, whereby monohydroxy compounds or dihydroxy compounds with large aryl groups, alkyl groups or aryl/alkyl groups are incorporated thus affording the hydrophobic modification. Preferred associative thickeners therefore are polyalkylene glycols that have been modified so as to be hydrophobic. The hydrophilic component is formed by polyoxyalkylene units, preferably polyoxyethylene units but also polyoxypropylene units or a mixture thereof. The hydrophobic component preferably consists of hydrocarbon groups, for example long-chain alkyl groups, alkylaryl groups or arylalkyl groups.

Particularly preferred associative thickeners are aminoplast-polyether copolymers that have been modified so as to be hydrophobic. For their structure and preparation the reader is referred to WO 96/40815. In WO 96/40815 are described water-dispersible or water-soluble copolymers obtained as the reaction products of acid-catalyzed polycondensation of an at least difunctional aminoplast monomers with an at least difunctional alkylene polyether and a monofunctional compound containing hydrophobic groups. Suitable aminoplasts are shown in FIG. 1 of WO 96/40815. Particularly preferred are the glycoluril derivatives of formula X of WO 96/40815. Suitable alkylene polyethers are shown in FIG. 2 of WO 96/40815. Preferred alkylene polyethers are the polyethylene oxide diols. These can have a degree of ethoxylation from 20 to 500, preferably from 50 to 350 and particularly from 100 to 250. Suitable monofunctional compounds with hydrophobic groups are those of formula XIV of WO 96/40815.

Associative thickeners that are suitable according to the invention are preferably selected from among the polymers of general formula (I)

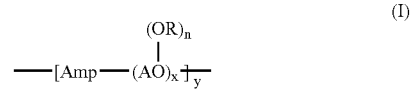

wherein Amp denotes an aminoplast monomer or a residue of an aminoplast oligomer or aminoplast polymer, AO stands for an alkylene oxide group, R denotes hydrogen, a $C_1-C_4$-alkyl group or a $C_1-C_4$-acyl group and x and y denote numbers greater than 1.

Particularly preferred are the reaction products of the acid-catalyzed polycondensation of (a) a glycoluril of general formula (II)

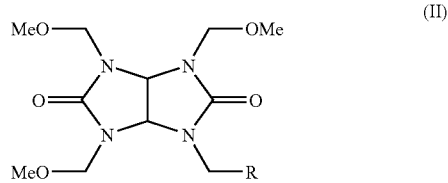

wherein R stands for H or preferably OMe, with (b) a polyethylene oxide diol having a degree of ethoxylation of 20 to 500, preferably 50 to 350 and particularly 100 to 250.

and (c) an optionally ethoxylated hydrophobic alcohol, alkylphenol, thiol, carboxamide, carbamate or hydrophobic carboxylic acid, as described on pages 17 to 19 of WO 96/40815. A particularly preferred glycoluril is 1,3,4,6-tetramethoxymethylglycoluril (TMMG).

Particularly suitable associative thickeners are those with INCI names polyether I, PEG-180/octoxynol-40/TMMG copolymer and PEG-180/laureth-50/TMMG copolymer, marketed, for example, by Süid-Chemie AG, Munich, Germany, under the tradenames Pure-Thix® HH, HL, L, M, TX-1442, TX-1450, TX-1451, TX-1452 and TX-1499.

Suitable fatty alcohols are, in principle, all saturated or unsaturated, branched or straight-chain fatty alcohols that are liquid at room temperature (about 25° C.). In particular, suitable fatty alcohols are decanol, undecanol, lauryl alcohol, 2-octyl-1-dodecanol, oleyl alcohol, linoleyl alcohol and linolenyl alcohol, among which lauryl alcohol, 2-octyl-1-dodecanol and oleyl alcohol are especially preferred.

The amount of fatty alcohol used in the colorant of the invention is preferably about 0.1 to 20 wt. % and particularly about 0.5 to 10 wt. %.

A suitable component (c) is a copolymer of PEG-150, a saturated methylenediphenyl diisocyanate and stearyl alcohol (INCI name: PEG 150/stearyl alcohol/SMDI copolymer), sold, for example, by ISP, Wayne, USA, under the tradename Aculyn 46. This thickener is preferably used in an amount from about 0.01 to 2 wt. % and particularly from about 0.05 to 1 wt. %.

The colorant of the invention preferably contains an oxidation dye precursor with which the coloration is produced by action of an oxidant, for example hydrogen peroxide, or in the presence of atmospheric oxygen.

Suitable oxidation dye precursors are, for example, the following developers, couplers and compounds coupling with themselves:

(i) Developers: 1,4-diaminobenzene (p-phenylenediamine); 1,4-diamino-2-methylbenzene (p-toluylenediamine); 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl)benzene; 2,5-diaminobiphenyl; 1,4-diamino-2-methoxymethylbenzene; 1,4-diamino-2-aminomethylbenzene; 1,4-diamino-2-hydroxymethylbenzene; 1,4-diamino-2-(2-hydroxyethoxy)-benzene; 2-[2-(acetylamino)ethoxyl]-1,4-diaminobenzene; 4-phenylaminoaniline; 4-dimethylaminoaniline; 4-diethylaminoaniline; 4-dipropylaminoaniline; 4-[ethyl-(2hydroxyethyl)amino]aniline; 4-[di(2-hydroxyethyl)amino]aniline; 4-[di(2-hydroxyethyl)amino]-2-methylaniline; 4-[(2-methoxyethyl)amino]aniline; 4-[(3-hydroxypropyl)amino]aniline; 4-[(2,3-dihydroxypropyl)amino]aniline; 1,4-diamino-2-(2-hydroxyethyl)benzene; 1,4-diamino-2-(1-methylethyl)benzene; 1,3-bis-[(4-aminophenyl)-(2-hydroxyethyl)amino]-2-propanol; 1,4-bis-[(4-aminophenyl)amino]butane; 1,8-bis(2,5-diaminophenoxy)-3,6-dioxaoctane; 4-aminophenol; 4-amino-3-methylphenol; 4-amino-3-(hydroxymethyl)phenol; 4-amino-3-fluorophenol; 4-methylaminophenol; 4-amino-2-(aminomethyl)phenol; 4-amino-2-(hydroxymethyl) phenol; 4-amino-2-fluorophenol; 4-amino-2-[(2-hydroxyethyl)amino]methylphenol; 4-amino-2-methylphenol; 4-amino-2-(methoxymethyl)phenol; 4-amino-2-(2-hydroxyethyl) phenol; 5-aminosalicylic acid; 2,5-diaminopyridine; 2,4,5,6-tetraaminopyrimidine; 2,5,6-triamino-4-(1H)-pyrimidone; 4,5-diamino-1-(2-hydroxyethyl)-1H-pyrazole; 4,5-diamino-1-1-(1-methylethyl)-1H-pyrazole; 4,5-diamino-1-[(4-methylphenyl)methyl]-1H-pyrazole; 1-[(4-chlorophenyl)methyl]-4,5-diamino-1H-pyrazole; 4,5-diamino-1-methyl-1H-pyrazole; 2-aminophenol; 2-amino-6-methylphenol and 2-amino-5-methylphenol, alone or in admixture with one another.

(ii) Couplers: N-(3-dimethylaminophenyl)urea; 2,6-diaminopyridine; 2-amino-4-[(2-hydroxyethyl)amino]anisole; 2,4-diamino-1-fluoro-5-methylbenzene; 2,4-diamino-1methoxy-5-methylbenzene; 2,4-diamino-1-ethoxy-5-methylbenzene; 2,4-diamino-1(2-hydroxyethoxy)-5-methylbenzene; 2,4-di[(2-hydroxyethyl)amino]-1,5-dimethoxybenzene; 2,3-diamino-6-methoxypyridine; 3-amino-6methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)benzene; 2,4diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diaminophenoxyacetic acid; 3-[di-(2-hydroxyethyl)amino]aniline; 4-amino-2-di[(2-hydroxyethyl)amino]-1-ethoxybenzene; 5-methyl-2-(1-methylethyl)phenol; 3-[(2-hydroxyethyl)amino]aniline; 3-[(2-aminoethyl)amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]acetamide; 5-[(2-hydroxyethyl)amino]-4methoxy-2-methylphenol; 5-[(2-hydroxyethyl)amino]-2-methylphenol; 3-[(2-hydroxyethyl)amino]phenol; 3-]( 2-methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxypyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1, 2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylenedioxyaniline; 5-[(2-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4(2H)-benzoxazine; 6-amino-3,4-dihydro-1,4[2H]benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione, alone or in admixture with one another.

(iii) Compounds coupling with themselves: 2-amino-5-methylphenol; 2-amino-6-methylphenol, 2-amino-5-ethoxyphenol or 2-propylamino-5-aminopyridine.

The total amount of the oxidation dye precursors contained in the colorant of the invention is from about 0.01 to 12 wt. % and particularly from about 0.2 to 6 wt. %.

To achieve certain color shades, the colorant may also contain common natural and/or synthetic direct dyes, for example vegetable dyes such as henna or indigo, triphenylmethane dyes, aromatic nitro dyes, azo dyes, quinone dyes or cationic or anionic dyes.

Suitable synthetic dyes are, for example, 1,4-bis[(2-hydroxyethyl)amino]-2-nitrobenzene; 1-(2-hydroxyethyl)amino-2-nitro-4-[di(2-hydroxyethyl)amino]benzene (HC Blue No. 2); 1-amino-3-methyl-4-[(2-hydroxyethyl)amino]-6-nitrobenzene (HC Violet No. 1); 4-[ethyl-(2-hydroxyethyl)amino]-1-[(2-hydroxyethyl)amino]-2-nitrobenzene hydrochloride (HC Blue No. 12); 4-[di(2-hydroxyethyl)amino)]-1-[(2-methoxyethyl)amino]-2-nitrobenzene (HC Blue No. 11); 1-[(2,3-dihydroxypropyl)amino]-4-[methyl-(2-hydroxyethyl)amino]-2nitrobenzene (HC Blue No. 10); 1-[(2,3-dihydroxypropyl)amino]-4-[ethyl-(2-hydroxyethyl)amino]-2-nitrobenzenehydrochloride (HC Blue No.9); 1-(3-hydroxypropylamino)-4-[di(2-hydroxyethyl)amino]-2-nitrobenzene(HC Violet No. 2); 1-methylamino-4-methyl-[2,3-dihydroxypropyl)amino]-2-nitrobenzene (HC Blue No. 6); 2-[(4-amino-2-nitrophenyl)amino]-5-dimethylaminobenzoic acid (HC Blue No. 13); 1-amino-4-[(2-hydroxyethyl)amino]-2-nitrobenzene (HC Red No, 7); 2-amino-4,6-dinitrophenol, 4-amino-2-nitrodiphenylamine (HC Red No. 1); 1-amino-4-[di(2-hydroxyethyl)amino]-2nitrobenzene hydrochloride (HC Red No. 13); 1-amino-5-chloro-4-[(2-hydroxyethyl)amino]-2-nitrobenzene; 4-amino-1-[(2-hydroxyethyl)amino]-2-nitrobenzene (HC Red No. 3); 4-amino-3-nitrophenol; 4-[(2-hydroxyethyl)amino]-3-nitrophenol, 1-[(2-aminoethyl)amino]-4-(2-hydroxyethoxy)-2-nitrobenzene (HC Orange No. 2); 4-(2,3-dihydroxypropoxy)-1-[(2-hydroxyethyl)amino]-2-nitrobenzene (HC Orange No. 3); 1-amino-5-chloro-4-[(2,3-dihydroxypropyl)amino]-2-nitrobenzene (HC Red No. 10); 5-chloro-1,4-[di(2,3-dihydroxypropyl)amino]-2-nitrobenzene (HC Red No. 11); 2-[(2-hydroxyethyl)amino]-4,6-dinitrophenol; 4-ethylamino-3-nitrobenzoic acid; 2-[(4-amino-2-nitrophenyl)amino]benzoic acid, 2-chloro-6-ethylamino-4-nitrophenol; 2-amino-6-chloro-4-nitrophenol: 4-[(3-hydroxypropyl)amino]-3-nitrophenol; 2,5-diamino-6-nitropyridine; 1,2,3,4-tetrahydro-6-nitroquinoxaline; 7-amino-3,4-dihydro-6-nitro-2H-1,4-benzoxazine (HC Red No. 14); 1-amino-2-[(2-hydroxyethyl)amino]-5-nitrobenzene (HC Yellow No, 5); 1-(2-hydroxyethoxy)-2-[(2-hydroxyethyl)amino]-5-nitrobenzene (HC Yellow No. 4); 1-[(2-hydroxyethyl)amino]-2-nitrobenzene (HC Yellow No. 2); 2-[(2-hydroxyethyl)amino]-1-methoxy-5-nitrobenzene; 2-amino-3-nitrophenol; 1-(2-hydroxyethoxy)-3-methylamino-4-nitrobenzene; 2,3-(dihydroxypropoxy)-3-methylamino-4-nitrobenzene, 2-[(2-hydroxyethyl)amino]-5-nitrophenol (HC Yellow No. 11); 3-[(2-aminoethyl)amino]-1-methoxy-4-nitrobenzene hydrochloride (HC Yellow No. 9); 1-[(2-ureidoethyl)amino]-4-nitrobenzene; 4-[(2,3-dihydroxypropyl)amino]-3nitro-1-trifluoromethylbenzene(HC Yellow No. 6); 1-chloro-2,4-bis[(2hydroxyethyl)amino]-5-nitrobenzene(HC Yellow No. 10); 4-[(2-hydroxyethyl)amino]-3-nitro-1-methylbenzene, 1-chloro-4-[(2-hydroxyethyl)amino]-3-nitrobenzene (HC Yellow No. 12); 4-[(2-hydroxyethyl)amino]-3-nitro-1-trifluoromethylbenzene (HC Yellow No. 13); 4-[(2-hydroxyethyl)amino]-3-nitrobenzonitrile (HC Yellow No. 14); 4-[(2-hydroxyethyl)amino]-3-nitrobenzamide (HC Yellow No. 15); 1,4-di[(2,3-dihydroxypropyl)amino]-9,10-anthraquinone; 1-[(2-hydroxyethyl)amino]-4-methylamino-9,10-anthraquinone (Cl 61505, Disperse Blue No. 3), 2-[(2-aminoethyl)amino]-9,10-anthraquinone (HC Orange No. 5); 1-hydroxy-4-[(4-methyl-2-sulfophenyl)amino]-9,10-anthraquinone, 1[(3-aminopropyl)amino]-4-methylamino-9, 10-anthraquinone (HC Blue No. 8); 1-[(3-aminopropyl)amino]-9,10-anthraquinone (HC Red No. 8); 1,4-diamino-2-methoxy-9,10-anthraquinine (Cl 62015, Disperse Red No. 11, Solvent Violet No. 26); 1,4-dihydroxy-5,8-bis[(2-hydroxyethyl)amino]-9,10-anthraquinone (Cl 62500 Disperse Blue No. 7, Solvent Blue No. 69); 9-(dimethylamino)benzo[a]-phenoxazin-7-ium chloride (Cl 51175; Basic Blue No. 6); di[4-(diethylamino)phenyl][4-(ethylamino)naphthyl]carbenium chloride (Cl 42595; Basic Blue No. 7); 3,7-di(dimethylamino)phenothiazin-5-ium chloride (Cl 52015, Basic Blue No. 9); di[4-(dimethylamino)phenyl][4-(phenylamino)naphthyl]carbenium chloride (Cl 44045; Basic Blue No. 26); 2-{[4-ethyl(2-hydroxyethylamino) phenyl]azo}-6-methoxy-3-methyl-benzothiazolium methylsulfate (Cl 11154; Basic Blue No. 41); 8-amino-2-bromo-5-hydroxy-4-imino-6-{[3-(trimethylammonio)phenyl]amino}-1-(4H)-naphthalenone chloride (Cl 56059; Basic Blue No. 99); bis[4-(dimethylamino)phenyl][4-(methylamino)phenyl]carbenium chloride (Cl 42535; Basic Violet No. 1); tris[4-(dimethylamino)phenyl]carbenium chloride (Cl 42555; Basic Violet No. 3); 2-[3,6-(diethylamino)dibenzopyranium-9-yl]benzoyl chloride (Cl 45170; Basic Violet No. 10); di(4-aminophenyl)(4amino-3-methylphenyl)carbenium chloride (Cl 42510; Basic Violet No. 14); 1,3-bis[(2,4-diamino-5-methylphenyl)azo]-3-methylbenzene (Cl 21010; Basic Brown No. 4); 1-[(4-aminophenyl)azo]-7-(trimethylammonio)-2-naphthol chloride (Cl 12250; Basic Brown No. 16); 1-[(4-amino-3-nitrophenyl)azo]-7-(trimethylammonio)-2-naphthol chloride (Cl 12251; Basic Brown No. 17); 3,7-diamino-2,8-dimethyl-5-phenylphenazinium chloride (Cl 50240; Basic Red No. 2); 1,4-dimethyl-5-{[4-(dimethylamino)phenyl]azo}-1,2,4-triazolium chloride (Cl 11055; Basic Red No 22); 2-hydroxy-1-[(2-methoxyphenyl)azo]-7-(trimethylammonio)naphthalene chloride (Cl 12245; Basic Red No. 76); 2-{2-[(2,4-dimethoxyphenyl)amino]ethenyl}-1,3,3-trimethyl-3H-indol-1-ium chloride (Cl 48055; Basic Yellow No. 11); 3-methyl-1-phenyl-4-{[3-(trimethylammonio)phenyl]azo}pyrazol-5-one chloride (Cl 12719; Basic Yellow No. 57); bis[4-(diethylamino)phenyl]phenylcarbenium hydrogen sulfate (1:1) (Cl142040; Basic Green No. 1); 1-[di(2-hydroxyethyl)amino]-3-methyl-4-[(4-nitrophenyl)azo]benzene (Cl 11210; Disperse Red No. 17); 4-[(4-aminophenyl)azo]-1-[di(2-hydroxyethyl)amino]-3-methylbenzene (HC Yellow No. 7); 2,6-diamino-3-[(pyridin-3-yl)azo]pyridine, disodium 6-hydroxy-5-[(4-sulfophenyl)azo]-2-naphthalenesulfonate (Cl 15985; Food Yellow No. 3; FD&C Yellow No. 6); disodium 2,4-dinitro-1-naphthol-7-sulfonate (Cl10316; Acid Yellow No. 1; Food Yellow No. 1); 2-(1,3-indandion-2-yl)quinolin-x,x-sulfonic acid (mixture of monosulfonic and disulfonic acid) (Cl 47005; D&C Yellow No. 10; Food Yellow No. 13; Acid Yellow No. 3); trisodium 5-hydroxy-1-(4-sulfophenyl)-4-[(4-sulfophenyl)azo]pyrazol-3-carboxylate (Cl 19140; Food Yellow No. 4; Acid Yellow No. 23); 9-(2-carboxyphenyl)-6-hydroxy-3H-xanthen-3-one (Cl 45350; Acid Yellow No. 73; D&C Yellow No. 8); sodium 5[(2,4-dinitrophenyl)amino]-2-phenylaminobenzenesulfonate (Cl 10385; Acid Orange No. 3); monosodium 4-[(2,4-dihydroxyphenyl)azo]benzenesulfonate (Cl 14270; Acid Orange No. 6); sodium 4-[(2-hydroxy-1-naphthyl)azo]benzenesulfonate (Cl 15510; Acid Orange No. 7); sodium 4-{2,4-dihydroxy-3[(2,4-dimethylphenyl)azo]phenyl}azobenzenesulfonate (Cl 20170; Acid Orange No. 24); disodium 4-hydroxy-3-[(4-sulfo-1-naphthyl)azo]-1-naphthalenesulfonate (Cl 14720; Acid Red No. 14); trisodium 6-hydroxy-5-[(4-sulfo-1-naphthyl)azo]-2,4-naphthalenedisulfonate (Cl 16255; Ponceau 4R; Acid Red No. 18); trisodium 3-hydroxy-4[(4-sulfo-1-naphthyl)azo]-2,7-naphthalenedisulfonate (CI 16185; Acid Red No, 27); disodium 8-amino-1-hydroxy-2-(phenylazo)-3,6-naphthalenedisulfonate (CI 17200; Acid Red No. 33); disodium 5-(acetylamino)-4-hydroxy-3-[(2-methyl-phenyl)azo]-2,7-naphthalenedisulfonate (CI 18065; Acid Red No. 35); disodium 2-(3-hydroxy-2,4,5,7-tetraiododibenzo-6-pyranon-9-yl)benzoate (CI 45430; Acid Red No. 51); N-[6-(diethylamino)-9-(2,4-disulfophenyl)-3H-xanthen-3-ylidene]-N-ethylethaneammonium hydroxide, inner salt, sodium salt (CI 45100; Acid Red No. 52); disodium 8-{[4-(phenylazo)phenyl]azo}-7-naphthol-1,3-disulfonate (CI 27290; Acid Red No. 73); 2',4',5',7'-tetrabromo-3',6'-dihydroxyspiro{isobenzofuran-1(3H),9'-[9H]xanthene}-3-one disodium salt (CI 45380; Acid Red No. 87); 2',4',5',7'-tetrabromo-4,5,6,7-tetrachloro-3',6'-dihydroxyspiro{isobenzofuran1(3H),9'[9H]xanthen}-3-one disodium salt (CI 45410; Acid Red No. 92); 3',6'-dihydroxy-4',5'-diiodospiro[isobenzofuran-1(3H),9'(9H)-xanthene]3-one disodium salt (CI 45425; Acid Red No. 95); (2-sulfophenyl)di{4(ethyl-[4-sulfophenylmethyl]amino}phenylcarbenium disodium salt, betaine (CI 42090; Acid Blue No. 9; FD&C Blue No. 1); 1,4-bis[(2-sulfo-4-methylphenyl)amino]-9,10-anthraquinone disodium salt (CI 61570; Acid Green No. 25); bis[4-(dimethylamino)phenyl]-(3,7-disulfo-2-hydroxy-1-naphthyl)carbenium inner salt, monosodium salt (CI 44090; Food Green No. 4; Acid Green No. 50); bis[4-(diethylamino)phenyl](2,4-disulfophenyl)carbenium inner salt, sodium salt (2:1) (CI 42045; Food Blue No. 3; Acid Blue No. 1); bis[4-(diethylamino)phenyl]-(5-hydroxy-2,4-disulfophenyl)carbenium inner salt, calcium salt (2:1) (CI 42051; Acid Blue No. 3); sodium 1-amino-4-(cyclohexylamino)-9,10-anthraquinone-2-sulfonate (CI 62045; Acid Blue No. 62); disodium 2-(1,3-dihydro-3-keto-5-sulfo-2H-indol-2-ylidene)-2,3-dihydro-3-keto-1H-indole-5-sulfonate (CI 73015; Acid Blue No. 74); 9-(2-carboxyphenyl)-3-[(2methylphenyl)amino]-6-[(2-methyl-4-sulfophenyl)amino]xanthilium inner salt, monosodium salt (CI 45190; Acid Violet No. 9); 1-hydroxy-4-[(4-methyl-2-sulfophenyl)amino]-9,10-anthraquinone sodium salt (CI 60730; D&C Violet No. 2; Acid Violet No. 43); bis{3-nitro-4-[(4-phenylamino)-3-sulfophenylamino]phenyl}sulfone (CI 10410; Acid Brown No. 13); disodium 5-amino-4-hydroxy-6-[(4-nitrophenyl)azo]-3-(phenylazo)-2,7-naphthalenedisulfonate (CI 20470; Acid Black No. 1); 3-hydroxy-4-[(2-hydroxy-1-naphthyl)azo]-7-nitro-1-naphthalenesulfonic acid chromium complex (3:2) (CI 15711; Acid Black No.52); disodium 3-[(2,4-dimethyl-5-sulfophenyl)azo]-4-hydroxy-1-naphthalenesulfonate (CI 14700; Food Red No. 1; FD&C Red No. 4; tetrasodium 4-(acetylamino)-5-hydroxy-6-{7-sulfo-4-[(4-sulfophenyl)azo]1-naphthylazo}-1,7-naphthalenedisulfonate (CI 28440; Food Black No. 1) and sodium 3-hydroxy-4-(3-methyl-5-keto-1-phenyl-4,5-dihydro-1H-pyrazol-4-ylazo)naphthalene-1-sulfonate, chromium complex (Acid Red No. 195), alone or in combination with one another.

The total quantity of direct dyes in the colorant of the invention amounts to about 0.01 to 7 wt. % and preferably about 0.2 to 4 wt. %.

Other common dyes known to be used for coloring hair and which can be contained in the colorant of the invention are described by, among others, E. Sagarin in pages 503 if, by H. Janistyn in, "Handbuch der Kosmetika und Riechstoffe" [Handbook of Cosmetics and Fragrance Materials"], vol. 3 (1973), pages 388 ff, and by K. Schrader in "Grundlagen und Rezepturen der Kosmetika" [Fundamentals and Formulations of Cosmetics], 2nd edition (1989), pages 782–815.

Although oxidation colorants are preferred, the colorant of the invention can, of course, also be used in the form of a non-oxidative colorant based on the aforesaid direct dyes.

Moreover, the colorant of the invention can contain antioxidants, for example ascorbic acid, thioglycolic acid or sodium sulfite, and complexing agents for heavy metals, for example an ethylenediaminetetraacetate or nitriloacetic acid, in an amount of up to about 0.5 wt. %. Perfume oils can be contained in the dye carrier composition of the invention in an amount of up to about 1 wt. %. Naturally, the aforedescribed hair colorant can optionally contain other additives commonly used in hair colorants, for example preservatives, antioxidants, for example sodium sulfite, thioglycolic acid or ascorbic acid; complexing agents, solvents such as water, the lower aliphatic alcohols, for example aliphatic alcohols with 1 to 4 carbon atoms, such as ethanol, propanol and isopropanol, or glycols such as glycerol and 1,2-propylene glycol; wetting agents or emulsifiers from the classes of anionic, cationic, amphoteric or nonionic surface-active substances; furthermore softeners, vaseline, silicone oil, paraffin oil and fatty acids, as well as hair-care agents such as cationic resins, lanolin derivatives, cholesterol, vitamins, pantothenic acid and betaine. The said constituents are used in amounts usually employed for such purposes, for example the wetting agents and emulsifiers at a concentration of 0.1 to 30 wt. % and the hair-care agents at a concentration of 0.1 to 5.0 wt. %. Particularly advantageous is the addition of a nonionic and/or anionic surfactant or emulsifier, for example a fatty alcohol sulfate, particularly lauryl sulfate and sodium cocoylsulfate, ethoxylated fatty alcohol sulfate, particularly a sodium lauryl ether sulfate with 2 to 4 ethylene oxide units in the molecule, ethoxylated fatty esters, ethoxylated nonylphenol, ethoxylated fatty alcohol, alkylbenzenesulfonate or fatty alkanolamide, in a total amount from about 0.1 to 30 wt. % and preferably from 0.2 to 15 wt. %.

For nonoxidative colorants based on direct dyes, the pH of the colorant of the invention is in the range from about 5 to 10 and preferably from 6 to 9, whereas for oxidative colorants based on oxidation dye precursors the pH is in the range from about 6 to 12 and preferably from 9 to 11. The pH of the ready-to-use oxidation hair colorant (namely of the mixture of the hair colorant of the invention and the oxidant) is from about 5.5 to 10 and preferably from 6 to 9.

Depending on the composition and the desired pH of the colorant, the pH is preferably adjusted with ammonia or an organic amine, for example glucamine, aminomethylpropanol, monoethanolamine or triethanolamine, with an inorganic base, for example sodium hydroxide, potassium hydroxide, sodium carbonate or calcium hydroxide, or with an organic or inorganic acid, for example lactic acid, citric acid, acetic acid or phosphoric acid.

The colorant of the invention is preferably packaged in the form of an aqueous or aqueous-alcohol formulation, for example as a thickened solution, or as an emulsion, cream or gel. In principle, however, it is also possible to thicken the colorant only just before use by addition of the 3-component combination of the invention.

When used for oxidative dyeing, the aforedescribed colorant is mixed with an oxidant just before use, and an amount of the ready-to-use mixture sufficient for dyeing, as a rule about 60 to 200 grams, is applied to the fibers.

If the colorant of the invention contains no oxidation dye precursors or if it contains oxidation dye precursors that are readily oxidized by atmospheric oxygen, said colorant can be applied to the keratin fibers directly without previous mixing with an oxidant.

Suitable oxidants for developing the coloration are primarily hydrogen peroxide or its compounds of addition to urea, melamine or sodium borate, in the form of a 1 to 12% and preferably 1.5 to 6% aqueous solution. The mixing ratio of colorant to oxidant depends on the concentration of the oxidant and as a rule is about 5:1 to 1:2 and preferably 1:1, the amount of oxidant in the ready-to-use composition being preferably about 0.5 to 8 wt. % and particularly 1 to 4 wt. %.

The ready-to-use colorant is allowed to act on the keratin fibers (for example human hair) at 15° to 50° C. for about 10 to 45 minutes and preferably for about 15 to 30 minutes after which the fibers are rinsed with water and dried. Optionally, following this rinsing, the keratin fibers are washed with a shampoo and possibly post-rinsed with a weak organic acid, for example tartaric acid. The keratin fibers are then dried.

If necessary, the viscosity of the oxidative colorant of the invention can readily be increased also after the mixing with the oxidant by addition of the combination of components (a) to (c) of the invention. This provides simpler and more economical basic formulations. It is also possible to thicken the colorant just before use (before, after or during the mixing with the oxidant) by addition of the combination of components (a) to (c) of the invention.

A colorant prepared to have the composition according to the invention meets in outstanding manner the requirements in terms of adhesion properties, application characteristics and viscosity adjustment and is appreciably easier to apply. Moreover, the colorants of the invention have a uniform consistency and are cosmetically appealing. Particularly notable is the very good viscosity and outstanding stability of the colorants of the invention and their excellent adhesion to hair. Furthermore, the use of the combination of the invention of (a) at least one nonionic, amphiphilic associative thickener, (b) at least one fatty alcohol that is liquid at 25° C. and (c) a PEG-150/stearyl alcohol/SMDI copolymer makes it possible to vary the weight ratio of colorant to oxidant over a wide range (for example from 1:1 to 1:2.5) without adversely affecting the viscosity and adhesion properties of the ready-to-use oxidation colorant in an appreciable manner.

The following examples are intended to explain the subject matter of the invention more closely without limiting its scope.

EXAMPLES

Example 1

Oxidation Hair Colorant, Liquid

| | |
|---|---|
| 0.2000 g | of PEG-180/laureth-50/TMMG copolymer [corresponds to 1 g of Pure Thix ® TX-1450 (20%), supplied by Süd Chemie/USA] |
| 0.2850 g | of PEG-150/stearyl alcohol/SMDI copolymer [corresponds to 1.5 g of Aculyn 46 (19%), supplied by ISP/USA] |
| 5.0000 g | of 2-octyl-1-dodecanol (Eutanol G, supplied by Cognis/Germany) |
| 15.0000 g | of oleic acid |
| 10.0000 g | of sodium lauryl alcohol diethylene glycol ether sulfate (28% aqueous solution) |
| 1.3620 g | of 4-aminophenol |
| 0.5000 g | of 1-naphthol |
| 0.0136 g | of resorcinol |
| 0.0034 g | of 2-amino-6-chloro-4-nitrophenol |
| 12.0000 g | of ammonia, 25% aqueous solution |
| 1.0000 g | of disodium ethylenediaminetetraacetate |
| 1.0000 g | of ascorbic acid |
| 15.0000 g | of isopropanol |
| to 100.0000 g | water |

Just before use, 50 g of the foregoing hair colorant was mixed with 50 g of a 6% aqueous hydrogen peroxide solution. This gave a homogeneous, cosmetically appealing, optimally thickened, colorant formulation. The mixture thus obtained was then applied to naturally blond hair. After an exposure time of 30 min at 40° C., the hair was rinsed with water and dried. The hair showed a bright copper-red coloration.

Example 2

Oxidation Hair Colorant for Coloration Brightening, in Gel Form

| Component (A): | Liquid Dye Carrier Composition |
|---|---|
| 0.50 g | of PEG-180/octoxynol-40/TMMG copolymer [corresponds to 2.5 g of Pure Thix ® L (20%), supplied by Süd Chemie/USA] |
| 0.60 g | of PEG-150/stearyl alcohol/SMDI copolymer [corresponds to 3.15 g of Aculyn 46 (19%), supplied by ISP/USA] |
| 10.00 g | of lauryl alcohol |
| 6.00 g | of nonylphenol ethoxylated with 4 moles of ethylene oxide |
| 6.00 g | of oleic acid |
| 0.50 g | of para-phenylenediamine |
| 0.07 g | of resorcinol |
| 5.00 g | of sodium lauryl alcohol diethylene glycol ether sulfate, 28% aqueous solution |
| 1.00 g | of disodium ethylenediaminetetraacetate |
| 18.00 g | of ammonia, 25% aqueous solution |
| 8.00 g | of ethanol |
| to 100 g | water |

| Component (B): | Hydrogen Peroxide Emulsion |
|---|---|
| 10.0 g | of cetylstearyl alcohol |
| 1.5 g | of cholesterol |
| 4.0 g | of sodium lauryl alcohol diethylene glycol ether sulfate, 28% aqueous solution |
| 35.0 g | of hydrogen peroxide, 35% aqueous solution |
| 0.3 g | of perfume |
| to 100.0 g | water |

Before use, 40 g of the liquid dye carrier composition (A) was mixed with 80 g of the hydrogen peroxide emulsion (B), corresponding to an (A):(B) mixing ratio of 1:2, and 120 g of this mixture was applied to gray human hair. After an exposure time of 20 min at room temperature, the hair was rinsed with water and dried. The hair treated in this manner was colored a uniform bright brown from hairline to hair tips. The colorant of the invention was easily applied and did not run off the hair.

Example 3

Oxidation Hair Colorant, in the Form of a Cream

| | |
|---|---|
| 0.10 g | of PEG-180/laureth-50/TMMG copolymer |

-continued

| | | |
|---|---|---|
| | | (Pure Thix ® TX-1450, supplied by Süd Chemie/USA) |
| 0.30 g | | of PEG-150/stearyl alcohol/SMDI copolymer [corresponds to 1.6 g of Aculyn 46 (19%), supplied by ISP/USA] |
| 3.00 g | | of oleyl alcohol |
| 15.00 g | | of cetyl alcohol |
| 3.50 g | | of sodium lauryl alcohol diethylene glycol ether sulfate (28% aqueous solution) |
| 3.00 g | | of monoethanolamine |
| 1.30 g | | of 1-methyl-2,5-diaminobenzene |
| 1.00 g | | of beeswax |
| 0.65 g | | of resorcinol |
| 0.50 g | | of keratin hydrolyzate |
| 0.50 g | | of silk protein hydrolyzate |
| 0.50 g | | of 2-amino-6-chloro-4-nitrophenol |
| 0.30 g | | of ascorbic acid |
| to 100.00 g | | water |

Just before use, 50 g of the foregoing hair colorant was mixed with 50 g of 12% aqueous hydrogen peroxide solution. The resulting mixture was then applied to naturally blond hair. After an exposure time of 30 min at 40° C., the hair was rinsed with water and dried. A uniform, strong brown shade was obtained.

Example 4

Hair Tinting (Non-oxidative)

| | |
|---|---|
| 1.8 g | of PEG-180/laureth-50/TMMG copolymer (Pure Thix ® TX-1450, supplied by Süd Chemie/Germany) |
| 0.95 g | of PEG-150/stearyl alcohol/SMDI copolymer [corresponds to 5.0 g of Aculyn 46 (19%), supplied by ISP/USA] |
| 6.0 g | of lauryl alcohol |
| 5.0 g | of sodium lauryl sulfate |
| 1.5 g | of 2-amino-6-chloro-4-nitrophenol |
| 1.0 g | of monoethanolamine |
| 1.0 g | of beeswax |
| 0.5 g | of keratin hydrolyzate |
| 0.3 g | of silk protein hydrolyzate |
| 0.2 g | of glycine |
| to 100.0 g | water |

A slightly gelled colorant composition was obtained which because of its outstanding viscosity characteristics was easily and uniformly applied and adhered well to the hair. After an exposure time of 20 min at 20° C., the hair was rinsed with luke-warm water, styled and dried. The hair treated in this manner showed a uniform, very lustrous gold-orange coloration.

Example 5

Oxidative Colorant, in the Form of a Cream

| | |
|---|---|
| Component (A): Dye Carrier Composition | |
| 2.0 g | of PEG-180/laureth-50/TMMG copolymer (Pure Thix ® TX-1450, supplied by Süd Chemie/USA) |
| 2.0 g | of PEG-150/stearyl alcohol/SMDI copolymer [corresponds to 10.5 g of Aculyn 46 (19%), supplied by ISP/USA] |
| 8.0 g | of 2-octyl-1-dodecanol (Eutanol G, supplied by Cognis/Germany) |

-continued

| | |
|---|---|
| 3.0 g | of sodium lauryl alcohol diethylene glycol ether sulfate (28% aqueous solution) |
| 2.8 g | of 2,5-diaminotoluene sulfate |
| 1.0 g | of resorcinal |
| 0.4 g | of m-aminophenol |
| 0.2 g | of 2-amino-4-(2'-hydroxyethylamino)anisole sulfate |
| 0.3 g | of ascorbic acid |
| 0.1 g | of ethylenediaminetetraacetic acid |
| 12.2 g | of ammonia, 25% aqueous solution |
| 2.0 g | of ethanol |
| to 100.0 g | water |
| Component (B): Hydrogen Peroxide - Emulsion | |
| 10.0 g | of cetylstearyl alcohol |
| 1.5 g | of cholesterol |
| 4.0 g | of sodium lauryl alcohol diethylene glycol ether sulfate, 28% aqueous solution |
| 17.0 g | of hydrogen peroxide, 35% aqueous solution |
| 0.3 g | of perfume |
| to 100.0 g | water |

Before use, 40 g of the liquid dye carrier composition (A) was mixed with 80 g of the hydrogen peroxide emulsion (B), corresponding to an (A):(B) mixing ratio of 1:2, and 120 g of this mixture was applied to human hair. After an exposure time of 20 min at room temperature, the hair was rinsed with water and dried. The hair treated in this manner was of a uniform, dark-brown shade. The colorant of the invention adhered very well to the hair without running off.

Example 6

Comparative Tests

The colorant of Example 1 was compared with three colorants not according to the invention.

Colorant 6.1: Colorant of Example 1 in which PEG-150/stearyl alcohol/SMDI copolymer was replaced with the same weight of PEG-180/laureth-50/TMMG copolymer.

Colorant 6.2: Colorant of Example 1 in which PEG-180/laureth-50/TMMG copolymer was replaced with the same weight of PEG-150/stearyl alcohol/SMDI copolymer.

Colorant 6.3: Colorant of Example 1 in which the fatty alcohol (2-octyl-1-dodecanol) was replaced with the same weight of a different fat component (oleic acid).

Whereas the colorant of the invention of Example 1 met all requirements in outstanding fashion (meaning that after the mixing with the oxidant it exhibited excellent viscosity, outstanding adhesion to the hair, uniform consistency, cosmetic appeal and outstanding application properties), the colorants not according to the invention were unsatisfactory in one or more respects.

Thus, colorant 6.1 not according to the invention while exhibiting good viscosity ran off the hair because of its poor adhesion characteristics.

Colorant 6.2 not according to the invention also had sufficient viscosity, but its cosmetic appeal was unsatisfactory because of its slimy consistency.

Colorant 6.3, after mixing with the oxidant, was water-thin and did not exhibit sufficient viscosity Unless otherwise indicated, all percentages in the present patent application are by weight.

The invention claimed is:

1. A colorant for keratin fibers based on oxidation dye precursors and/or direct dyes, said colorant containing a combination of (a) at least one nonionic, amphiphilic associative thickener, (b) at least one fatty alcohol that is liquid at 25° C. and (c) a PEG-150/stearyl alcohol/SMDI copolymer in a suitable cosmetic carrier:

wherein said at least one nonionic, amphiphilic associative thickener is selected from the group consisting of polyether-1, PEG-180/octoxynol-40/TMMG copolymer, and PEG-180/laureth-50/TMMG copolymer; and wherein the at least one fatty alcohol is selected from the group consisting of decanol, undecanol, lauryl alcohol, 2-octyl-1-dodecanol, oleyl alcohol, linoleyl alcohol, and linolenyl alcohol.

2. The colorant as defined in claim 1, containing from 0.01 to 2.5 wt. % of said at least one nonionic, amphiphilic associative thickener.

3. The colorant as defined in claim 1, containing said at least one fatty alcohol in an amount from 0.1 to 20 wt. %.

4. The colorant as defined in claim 1, containing from 0.01 to 2 wt. % of the PEG-150/stearyl alcohol/SMDI copolymer.

5. The colorant as defined in claim 1, containing from 0.01 to 12 wt. % of the oxidation dye precursors and an oxidant that is mixed in immediately prior to use.

6. The colorant as defined in claim 1, containing from 0.01 to 12 wt. % of the oxidation dye precursors, and wherein said oxidation dye precursors comprise oxidizable precursors that are oxidized by atmospheric oxygen.

7. A ready-to-use oxidative hair colorant containing an oxidant, at least one oxidation dye precursor and a combination of from 0.1 to 2.5 wt. % of at least one nonionic, amphiphilic associative thickener; from 0.1 to 20 wt. % of at least one fatty alcohol that is liquid at 25° C. and from 0.01 to 2 wt.% of PEG-150/stearyl alcohol/SMDI copolymer, in a medium suitable for coloring hair;

wherein said at least one nonionic, amphiphilic associative thickener is selected from the group consisting of polyether-1, PEG-180/octoxynol-40/TMMG copolymer, and PEG-180/laureth-50/TMMG copolymer; and wherein the at least one fatty alcohol is selected from the group consisting of decanol, undecanol, lauryl alcohol, 2-octyl-1-dodecanol, oleyl alcohol, linoleyl alcohol, and linolenyl alcohol.

8. The colorant as defined in claim 1, containing from 0.01 to 7 wt. % of at least one of the direct dyes.

9. The colorant as defined in claim 1, further comprising at least one cosmetic additive ingredient selected from the group consisting of solvents, anionic surfactants, cationic surfactants, nonionic surfactants, amphoteric surfactants, antioxidants, complexing agents for heavy metals, perfume oils, preservatives, softeners, petrolatum, silicone oil, paraffin oil, fatty acids, cationic resins, lanolin, lanolin derivatives, cholesterol, vitamins, pantothenic acid and betaine.

10. The colorant as defined in claim 1, wherein the oxidation dye precursors comprise at least one developer and at least one coupler or at least one self-coupling oxidation dye compound.

11. The colorant as defined in claim 10, wherein said at least one developer is selected from the group consisting of 1,4-diaminobenzene; 1,4-diamino-2-methylbenzene; 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)-benzene; 1,4-diamino-2-(pyridin-3-yl) benzene; 2,5-diaminobiphenyl; 1,4-diamino-2-methoxymethylbenzene; 1,4-diamino-2-aminomethylbenzene; 1,4-diamino-2-hydroxymethyl-benzene; 1,4-diamino-2-{2-hydroxyethoxy}-benzene; 2[2-{acetylamino}ethoxy]-1,4-diaminobenzene; 4-phenylaminoaniline; 4-dimethylaminoaniline; 4-diethylamino-aniline; 4-dipropylaminoaniline; 4-[ethyl-(2hydroxyethyl)amino]aniline; 4-[di(2-hydroxy-ethyl)amino]aniline; 4[di(2hydroxyethyl) amino]-2-methylaniline; 4-[(2-methoxyethyl)-amino] aniline; 4[(3hydroxypropyl)amino]aniline; 4-[(2, 3-dihydroxypropyl)amino]aniline; 1,4-diamino-2-(2-hydroxyethyl)benzene; 1,4-diamino-2-(1-methylethyl)benzene; 1,3-bis-[(4-aminophenyl)-(2hydroxyethyl)amino]-2-propanol; 1,4-bis-[(4-aminophenyl)amino]butane; 1,8-bis-(2,5-diaminophenoxy)-3,6-dioxaoctane; 4-aminophenol; 4amino-3-methylphenol; 4amino-3-(hydroxymethyl)phenol; 4-amino-3-fluorophenol; 4-methylaminophenol; 4-amino-2-(aminomethyl)-phenol; 4-amino-2-(hydroxymethyl)phenol; 4-amino-2-fluorophenol; 4-amino-2-[(2-hydroxyethyl)-amino]methylphenol; 4-amino-2-methylphenol; 4amino-2-(methoxymethyl)phenol; 4amino2-(2-hydroxyethyl)phenol; 5-aminosalicylic acid; 2,5-diaminopyridine; 2,4,5,6-tetraaminopyrimidine; 2,5,6-triamino-4-(1H)-pyrimidone; 4,5-diamino-1-2-hydroxyethyl)-1H-pyrazole; 4,5-diamino-1-(1-methylethyl)-1H-pyrazole; 4,5-diamino-1-[(4-methylphenyl)methyl]-1H-pyrazole; 1-[(4-chlorophenyl) methyl]-4,5-diamino-1H-pyrazole; 4,5-diamino-1-methyl-1H-pyrazole; 2-aminophenol; 2amino-6-methylphenol and 2amino-5-methylphenol.

12. The colorant as defined in claim 10, wherein said at least one coupler is selected from the group consisting of N-(3dimethylaminophenyl)urea; 2,6-diamino-pyridine; 2amino-4[(2hydroxyethyl)amino]anisole; 2,4-diamino-1-fluoro-5-methyl-benzene; 2,4-diamino-1methoxy-5-methylbenzene; 2,4-diamino-1-ethoxy-5-methyl-benzene; 2,4-diamino-1-(2-hydroxyethoxy)-5-methylbenzene; 2,4-di[(2-hydroxyethyl)-amino]-1,5-dimethoxybenzene; 2,3-diamino-6-methoxypyridine; 3-amino-6-methoxy-2-(methylamino) pyridine; 2,6-diamino-3,5-dimethoxypyridine; 3,5diamino-2,6-dimethoxy-pyridine; 1,3-diaminobenzene; 2,4-diamino-1-(2-hydroxyethoxy)benzene; 1,3-diamino-4-(2,3-dihydroxypropoxy)benzene; 2,4-diamino-1,5-di(2-hydroxyethoxy)benzene; 1-(2-aminoethoxy)-2,4-diaminobenzene; 2-amino-1-(2-hydroxyethoxy}-4-methylaminobenzene; 2,4-diaminophenoxyacetic acid; 3-[di-{2-hydroxyethyl}amino]aniline; 4-amino-2-di-[(2-hydroxyethyl)amino]-ethoxybenzene; 5-methyl-2-(1-methylethyl)-phenol; 3-[{2-hydroxyethyl}amino]aniline; 3-[(2-aminoethyl)amino]aniline; 1,3-di(2,4-diaminophenoxy]propane; di(2,4-diaminophenoxy)methane; 1,3-diamino-2,4-dimethoxybenzene; 2,6-bis(2-hydroxyethyl)aminotoluene; 4-hydroxyindole; 3-dimethyl-aminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]-acetamide; 5-[(2-hydroxy-ethyl)amino]-4-methoxy2-methylphenol; 5-[(2-hydroxyethyl)amino]-2-methylphenol; 3-[(2-hydroxyethyl)amino]phenol; 3-[(2-methoxyethyl)amino]phenol; 5-amino-2-ethyl-phenol; 5-amino-2-methoxyphenol; 2-(4-amino-2-hydroxyphenoxy)-ethanol; 5-[(3-hydroxypropyl) amino]-2-methylphenol; 3-[(2,3-dihydroxypropyl)amino]-2-methylphenol; 3-[(2-hydroxyethyl)amino]-2-methylphenol; 2-amino-3-hydroxypyridine; 5-amino-4-chloro-2-methylphenol; 1-naphthol; 2-methyl-1-naphthol; 1,5-dihydroxy-naphthalene; 1,7-dihydroxynaphthalene; 2,3-dihydroxynaphthalene; 2,7-dihydroxy-naphthalene; 2-methyl-1-naphthol acetate; 1,3-dihydroxybenzene; 1-chloro-2, 4-dihydroxybenzene; 2-chloro-1,3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4- methylenedioxyphenol; 3,4-methylenedioxyaniline; 5-[(2-hydroxyethyl)-amino]-1,3-benzodioxole; 6-bromo-1-hydroxy-3,4-methylenedioxybenzene; 3,4-diaminobenzoic acid; 3,4-dihydro-6-hydroxy-1,4(2H)-benzoxazine; 6-amino-3,4-dihydro- 1,4[2H]-benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

13. The colorant as defined in claim 10, wherein said at least one self-coupling oxidation dye compound is selected from the group consisting of 2-amino-5-methyl-phenol; 2-amino-6-methylphenol; 2-amino-5-ethoxyphenol and 2-propylamino-5-aminopyridine.

* * * * *